United States Patent [19]

Coull et al.

[11] Patent Number: 5,527,675

[45] Date of Patent: Jun. 18, 1996

[54] METHOD FOR DEGRADATION AND SEQUENCING OF POLYMERS WHICH SEQUENTIALLY ELIMINATE TERMINAL RESIDUES

[75] Inventors: James M. Coull, Westford, Mass.; Leif Christensen, Valby, Denmark

[73] Assignee: Millipore Corporation, Bedford, Mass.

[21] Appl. No.: 109,548

[22] Filed: Aug. 20, 1993

[51] Int. Cl.$^6$ .............................. C12Q 1/68; C07H 21/00
[52] U.S. Cl. .................................. 435/6; 435/4; 435/18; 435/195; 435/212; 435/227; 435/228; 436/63; 436/86; 436/94; 530/402; 536/18.7; 536/25.3; 935/76; 935/77; 935/78; 935/88
[58] Field of Search ................................... 435/195, 212, 435/219, 227, 228, 4, 18, 6; 436/63, 905, 86, 94; 530/402; 536/18.7, 25.3; 935/76, 77, 78, 88

[56] References Cited

U.S. PATENT DOCUMENTS 5,011,861   4/1991   Coull et al. ............................... 521/53

FOREIGN PATENT DOCUMENTS 9220702   11/1992   WIPO .
9220703   11/1992   WIPO .
9312129    6/1993   WIPO .

OTHER PUBLICATIONS

Nielsen et al., Sequence—Selective Recognition of DNA by Strand Displacement with Thymine–Substituted Polyamide, Dec. 6, 1991, pp. 1497–1500 Science.
Stryer. L., Biochemistry, W. H. Feeman & Co., San Francisco, pp. 591–93, 1981.
Gait M. J. Oliyonucleotide Synthesis, IRL Press, New York pp. 135–36, 1991.
Christensen et al., Optimized Solid–Phase Synthesis of PNA Oligomers, Jun. 20, 1993, Poster #7, Thirteenth American Peptide Symposium, Edmonton, Canada.
Gross, E. et al., The Peptide, Academic Press, New York, pp. 100–118, 1980.
Egholm, M. et al., Recognition of Guanine and Adenine in DNA by Cytosine and Thymine Containing Peptide Nucleic Acids (PNA), 1992, pp. 9677–78, J. Am. Chem. Soc.
Stryer, L., Biochemistry, W. H. Freeman & Co., San Francisco, pp. 24–27 1981.
Inglis A. S. Chemical Procedures for C–terminal Sequencing of Peptides and Proteins, 1991, pp. 183–96, Analytical Biochemistry.
Chait, B. T. et al., Weighing Naked Proteins: Practical, High–Accuracy Mass Measurement of Peptides and Proteins, 1992 pp. 1885–94.
Rempp et al., Polymer Synthesis, Huthig & Wepf, New York New York, p. 202, 1991.
Bovey et al. Macromolecules: An Introduction to Polymer Science, 1979, pp. 48–49 and 238–41, New York.

Primary Examiner—W. Gary Jones
Assistant Examiner—Ardin H. Marschel
Attorney, Agent, or Firm—Testa, Hurwitz & Thibeault

[57] ABSTRACT

A method and apparatus for sequentially degrading at least a portion of a polymer of backbone repeating units, the polymer having a terminal repeating unit comprised of a nucleophile and a backbone carbonyl carbon distant from the nucleophile, comprising the steps of first initiating attack of said nucleophile upon said backbone carbonyl carbon by raising the energy level to activate said nucleophile for said attack. Secondly, forming a ring comprising the terminal repeating unit, thereby simultaneously releasing the ring and generating a shortened polymer having a terminal repeating unit capable of nucleophile attack upon the backbone carbonyl carbon and, lastly, maintaining the reaction conditions necessary for repeating steps a and b until the portion of the polymer desired is degraded. In a related embodiment, polyamide nucleic acid (PNA) sequences can be determined by generating a nested set of polymer fragments, each fragment having N-x repeating units where N is the total number of repeating units in the parent polymer and x is the number of degradation cycles the fragment has been subjected to, and then analyzing the nested set of polymer fragments to determine polymer sequence. An apparatus embodying the method of sequential degradation is also described. Analysis may be by MALD-TOF.

33 Claims, 5 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="Peptide nucleic acid"

( i x ) FEATURE:
( A ) NAME/KEY: misc_feature
( B ) LOCATION: 1..10
( D ) OTHER INFORMATION: /product="PNA Sequence Number 1"

( x i ) SEQUENCE DESCRIPTION: SEQ ID NO:1:

T T T T C C T C T C                                                                                                  1 0

( 2 ) INFORMATION FOR SEQ ID NO:2:

( i ) SEQUENCE CHARACTERISTICS:
( A ) LENGTH: 7 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="Peptide Nucleic Acid"

( i x ) FEATURE:
( A ) NAME/KEY: misc_feature
( B ) LOCATION: 1..7
( D ) OTHER INFORMATION: /product="PNA Sequence Number 2"

( x i ) SEQUENCE DESCRIPTION: SEQ ID NO:2:

T G A C T T T                                                                                                        7

METHOD FOR DEGRADATION AND SEQUENCING OF POLYMERS WHICH SEQUENTIALLY ELIMINATE TERMINAL RESIDUES

BACKGROUND

1. Field of the Invention

This invention generally relates to the field of polymer and synthetic nucleic acids chemistry. In particular, the invention concerns the degradation and sequence determination of polymers, particularly peptide nucleic acids (PNAs) which sequentially eliminate terminal residues.

2. Description of the Background Art

Peptide nucleic acids (PNAs) are recently discovered synthetic polyamides which are promising candidates for the sequence-specific regulation of DNA expression and for the preparation of gene targeted drugs. See European Patent applications EP 92/01219 and 92/01220. PNAs are biopolymer hybrids which possess a peptide-like backbone to which the nucleobases of DNA are attached. Specifically, PNAs are synthetic polyamides comprised of repeating units of the amino acid, 2-aminoethylglycine to which adenine, cytosine, guanine and thymine are attached through a methylene carbonyl group. The polymers are neutral in charge and water soluble. Complementary sequences of PNA bind to DNA with high specificity to give both double and triple helical forms. Surprisingly, PNA-DNA hybrids are more stable than the native double stranded DNA. Consequently, PNAs are promising candidates for application to the multifaceted field of DNA manipulation. See Nielsen, Peter E., et al., Science 254: 1497–1500 (1991). There is presently no known technique for sequencing PNA once it has been synthesized.

DNA, polypeptides and proteins are naturally occurring biopolymers which can be routinely sequenced by well understood methods. Because PNA is a hybrid biopolymer possessing both nucleic acid and polypeptide-like structure, it is logical to evaluate DNA and protein sequencing methods for application to the sequencing of PNA.

DNA may be sequenced by either the Maxam & Gilbert or Sanger sequencing methods. See Stryer, L., *Biochemistry*, W. H. Freeman and Co., San Francisco (1981) pp. 591–93. Additionally, short DNA oligomers have been sequenced by the mobility-shift (wandering spot) method. See Gait, M. J. *Oligonucleotide Synthesis*, IRL Press, NY (1990) pp. 135–36. Polypeptides and proteins are sequenced from their amine terminus by Edman degradation. See Stryer, L., *Biochemistry*, W. H. Freeman and Co., San Francisco (1981) pp. 24–27. Further, several new methods have been described for carboxy terminal sequencing of polypeptides. See Inglis, A. S., Anal. Biochem. 195:183–96 (1991). Moreover, the sequencing of polypeptides has also been described by generating a nested (sequence defining) set of fragments followed by mass analysis. See Chait, Brian, T. et al., Science 257:1885–94 (1992). However, as discussed in more detail below, these techniques cannot be used to sequence PNA because it is a hybrid biopolymer containing a non-naturally occurring polyamide backbone.

DNA is a biopolymer comprised of a deoxyribose phosphate backbone to which adenine, cytosine, guanine and thymine are attached. Both the Maxam & Gilbert and Sanger sequencing methods require the generation of a nested set of polymer fragments which are separated and analyzed to determine sequence. However, the deoxyribose phosphate backbone does not sequentially degrade by any known chemical method. Consequently, the nested set of polymer fragments is generated by alternative methods.

"Nested set" is a term used in the art of sequencing to define a partially degraded/synthesized sample of polymer used to determine the polymer sequence. Ideally, the nested set contains measurable quantities of each of the possible fragments generated by a degradation/synthesis process whereby analysis of the set of fragments will define the sequence. Therefore, all of the fragments have a common terminus, but the opposite terminus is determined by the point of backbone cleavage or synthesis termination. Consequently, the relative difference in length/mass of all shortened polymers is dependent upon the point of backbone cleavage or synthesis termination.

The Maxam & Gilbert method uses chemical reagents to cleave the deoxyribose phosphate backbone thereby generating a nested set of fragments. Alternatively, Sanger uses enzymatic methods to synthesize the nested set. Using the DNA to be sequenced as a template, a primer is annealed and a polymerase reaction proceeds in four separate vessels. Each vessel contains a different dideoxy nucleotide which terminates chain extension upon incorporation thereby generating a nested set of polymer fragments. Finally, the mobility-shift (wandering spot) method for DNA sequencing involves the use of a phosphodiesterase enzyme which randomly cleaves the deoxyribose phosphate backbone, thereby generating a nested set of polymer fragments.

These methods cannot be adapted to sequencing PNA. Because PNA is comprised of a polyamide backbone, the chemical treatments described by Maxam & Gilbert will not cleave PNA. Likewise, PNA is not amenable to Sanger sequencing because it is not a substrate for the enzyme DNA polymerase. Moreover, PNA is not a substrate for the phosphodiesterase enzymes used to degrade DNA for mobility-shift (wandering spot) analysis. Thus, no known DNA sequencing method will generate a nested set of PNA fragments suitable for separation and analysis.

The related art of protein sequencing is also of no assistance in trying to sequence PNA. Proteins and polypeptides are polyamides formed from the 20 naturally occurring amino acids. The sequence may be determined using amino or carboxy terminal sequencing methods. Protein sequencing generally involves the chemically induced sequential removal and identification of the terminal amino acid residue. Because there is no requirement that a nested set of polymer fragments be generated, typical protein sequencing methods differ substantially from DNA sequencing techniques.

Edman degradation requires that the polyamide have a free amino group which is reacted with an isothiocyanate. See Stryer, L., *Biochemistry*, W. H. Freeman and Co., San Francisco (1981) pp. 24–27. The isothiocyanate is typically phenyl isothiocyanate. The adduct intramolecularly reacts with the nearest backbone amide group of the polymer thereby forming a five membered ring. This adduct rearranges and the terminal amino acid residue is then cleaved using strong acid. The released phenylthiohydantoin (PTH) of the amino acid is identified and the shortened polymer can undergo repeated cycles of degradation and analysis.

Carboxy terminal sequencing methods mimic Edman degradation but involve sequential degradation from the opposite end of the polymer. See Inglis, A. S., Anal. Biochem. 195:183–96 (1991). Like Edman degradation, the carboxy-terminal sequencing methods involve chemically induced sequential removal and identification of the terminal amino acid residue.

Though PNA contains a polyamide backbone, protein sequencing chemistries would not be expected to degrade the polymer. The PNA backbone is non-naturally occurring and the repeating unit is substantially different than a polypeptide backbone. Thus, the chemical methods employed for protein degradation and sequencing should not degrade or be useful to sequence PNA.

More recently, polypeptide sequencing has been described by preparing a nested set (sequence defining set) of polymer fragments followed by mass analysis. See Chait, B. T. et al., Science 257:1885–94 (1992). Sequence is determined by comparing the relative mass difference between fragments with the known masses of the amino acid residues. Though formation of a nested (sequence defining) set of polymer fragments is a requirement of DNA sequencing, this method differs substantially from the conventional protein sequencing method consisting of sequential removal and identification of each residue. Nonetheless, Edman chemistry is still required for the formation of the nested set. Consequently, PNA cannot be sequenced by this method because PNA will not sequentially degrade by Edman degradation.

Synthetic polymers also decompose by depolymerization (also known as "depropagation" or "chain unzipping"). See Rempp et al., *Polymer Synthesis*, Huthig and Wepf Verlag, New York, (1991) p. 202. The process is common to polymerizations occurring by a free radical mechanism. Depolymerization regenerates the monomer by the spontaneous reversal of the polymerization reaction. Though depolymerization is a stepwise degradation of the polymer, it is a random equilibrium process which is too rapid to control or manipulate for sequence analysis. Moreover, PN As in particular are not assembled by free radical polymerization and have not been shown to degrade by this mechanism.

Synthetic polymers undergo intramolecular reactions known as "backbiting", but these processes do not degrade the polymer. See Bovey et al., *Macromolecules; an introduction to polymer science*, Academic Press, New York, (1979), pp.48–49 & 238–41. During free radical polymerizations, backbiting occurs by the intramolecular transfer of a free radical from the terminus of the growing polymer chain to an internal atom. Chain propagation continues from this point and the polymer becomes branched. Nonetheless, since PNAs are not assembled by free radial polymerization they will not degrade by this mechanism.

Reshuffling of formed polymers may occur by other backbiting processes. See Rempp et al., *Polymer Synthesis*, Huthig and Wepf Verlag, New York, (1991) p. 51. Polyesters which possess a hydroxyl terminus will intramolecularly attack at the ester groups of the polymer backbone. Additionally, polyamides having amino termini will attack at amide groups of the polymer backbone. Backbiting under these conditions results in polymer reshuffling. Because no fragment is lost, the mass of a polymer is not altered. Moreover, backbiting has been observed in PNA. Intramolecular attack of the terminal amino group of PNA upon a side chain amide group has been described. See Christensen, L. et al., *Optimized Solid-Phase Synthesis of PNA Oligomers*. Thirteenth American Peptide Symposium, Poster No.7, Jun. 20–23, 1993, Edmonton Canada. Also See FIG. 1 of this application, attack 1. The result is a rearrangement known as an N-acyl shift. Though PNA does rearrange through backbiting, this process will not yield a sequencing method because the mass of the polymer remains unchanged.

Presently, sequence information for PNA is only available from the actual synthetic procedure. Methods have been described for the synthesis of PNA monomers. See the aforementioned European Patent applications EP 92/01219 and 92/01220. Using conventional boc/benzyl protection chemistries for peptide synthesis, polymers are assembled by the sequential reaction of the amino terminus of the growing polymer with the carboxyl terminus of the next monomer. See Gross, Erhard et al., *The Peptide,* Academic Press, NY (1980) pp 100–118. The completely assembled polymer is deprotected and the crude sample analyzed. Analysis is typically comprised of a separations step followed by mass spectrometry of the isolated fragments. Separations analysis (e.g. High Performance Liquid Chromatography (HPLC), Capillary Liquid Chromatography or Capillary Electrophoresis) yields the number of components and relative amounts of each. For shorter oligomers, these techniques may be used to determine the length (number of repeating monomer units) of the polymer. However, no sequence information is generated. Thus, if the polymer is improperly assembled such that it is of proper length but the order of assembly is incorrect, separations analysis may not detect this aberration. Moreover, separations analysis cannot absolutely identify an isolated polymer.

Mass spectrometry is very effective when used to analyze PNA isolated from a separations process because it gives the exact mass of the purified polymer. The desired product is identified because other components have a mass differing from the expected mass. However, polymers having the correct monomer composition but differing in sequence cannot be differentiated because they will have the same mass as the desired product. This situation would occur if the order of assembly was incorrect. Thus, it is impossible to confirm the sequence of a PNA using only mass spectrometry.

It is critical that the sequence of a PNA be known with certainty otherwise experimental results may be misleading. Studies show that single base pair mismatches affect PNA-DNA binding. See Egholm, M. et al., J. Am. Chem. Soc. 114:9677–78 (1992). Because errors can be made during the chemical assembly of the polymer, methods suitable for the absolute confirmation of the sequence of the assembled PNA are desirable. Additionally, as a therapeutic agent, PNA must be fully characterized prior to acceptance for use in humans. Consequently, a sequencing method for PNA is required because it will give absolute confirmation of primary polyamide structure.

SUMMARY OF THE INVENTION

This invention includes a novel method and apparatus for the degradation of polymers which sequentially release terminal repeating units (residues). In general the polymers which may degrade by the method of this invention are PNAs, polyamides, polyesters and polythioesters. Specifically, the polymers are comprised of both terminal repeating units and backbone repeating units. At least one terminal repeating unit contains a terminal nucleophile (amino, hydroxyl or thiol group) and a backbone carbonyl carbon distant from the terminal nucleophile. Preferably, the terminal repeating units are derivatives of 2-aminoethylglycine, 2-hydroxyethylglycine or 2-thioethylglycine.

By the method of this invention the polymer degrades by repeated release of the terminal repeating unit (terminal residue) of the polymer. Degradation involves initiating the intramolecular attack of the terminal nucleophile of the polymer at the backbone carbonyl carbon at least 4 atoms distant from the nucleophile. Initiation of terminal nucleophilic attack requires raising the energy level of the system. The terminal repeating unit forms a stable ring structure which simultaneously releases from the polymer, thereby generating a shortened polymer having a terminal repeating unit comprised of a nucleophile (amino, hydroxyl, or thiol functional group) and backbone carbonyl carbon. Because the shortened polymer contains all of the functional groups necessary, given that the reaction conditions are maintained, the cycle will repeat on the shorted polymer until the desired portion is degraded or the sample is put below the activation energy of the decomposition reaction.

Whereas this invention includes a method for degrading a polymer sequentially, it also provides a method of sequencing the polymer. The method of this invention may be used to partially degrade a sample of polymer thereby generating a nested set of polymer fragments. The nested set of polymer fragments is then subjected to analysis. Generally, analysis consists of mass analysis obtained by mass spectroscopy. Preferably, mass analysis is by matrix assisted laser desorption time-of-flight (maLD-TOF) mass spectroscopy. The terminal repeating unit released to generate each sequentially degraded polymer fragment is then identified by comparison of the mass differences between polymer fragments. By analysis of this data the sequence of the polymer is determined.

It is an object of this invention to sequentially degrade peptide nucleic acids (PNAs), polyamides, polyesters and polythioesters.

It is another object of this invention to determine the sequence of PNAs, polyamides, polyesters and polythioesters.

It is a further object of this invention to provide an apparatus for determining the sequence of PNAs, polyamides, polyesters and polythioesters.

DETAILED DESCRIPTION OF THE INVENTION

The applicants have discovered that, under certain controlled situations, PNAs, polyamides, polyesters and polythioesters undergo sequential degradation by repeated release of the terminal repeating unit of the polymer. This was a surprising result, considering that no method was known for degrading synthetic polymers of this type. In one embodiment of this method, a nested set of polymer fragments is generated, through mass analysis of which the polymer is sequenced. In another embodiment, one may determine the sequence of a PNA which has been isolated from a PNA library because it exhibits binding to a molecule of interest during a screening assay. In still another embodiment, the polymer may form a bioerrodable matrix which releases chemical agents in a controlled manner determined by the rate of decomposition (degradation) of the polymer. The chemical agent may be entrapped by the polymer matrix or be a product of polymer degradation. In a further embodiment, the polymers may be used as biodegradable materials which are partially or completely degraded by the method of this invention once their utility has been exhausted. For example, used materials manufactured from PNAs, polyamides, polyesters, or polythioesters would be degraded for disposal by the method of this invention.

This invention is a method for the sequential degradation of a polymer. Polymers which degrade by the method of this invention are comprised of two (2) terminal repeating units and p backbone repeating units wherein p is an integer from 1–1,000,000. All repeating units are linked together by functional linkages thereby forming a polymer backbone. The functional linkages are selected from the group consisting of amide, ester and thioester. The terms "backbone", "repeating units" and "functional linkages" are given their usual meaning in the field of polymer chemistry. The polymers may be heterogeneous in backbone composition thereby containing any possible combination of amide, ester and thioester functional linkages. In a preferred embodiment the polymers are homogeneous in backbone composition and are polyamides, polyesters or polythioesters. In the most preferred embodiment, the polymer is a peptide nucleic acid (PNA).

The terminal repeating units are the same or different wherein at least one terminal repeating unit contains a terminal nucleophile and a backbone carbonyl carbon at least 4 atoms distant from the nucleophile. The terminal nucleophile is an amino, hydroxyl or thiol group. There are p backbone repeating units and in PNA, all are six atoms in length. All repeating units have a heteroatom or alkylated heteroatom at one terminus and a carbonyl carbon at the other terminus. Preferred repeating units are 2-aminoethylglycine, 2-hydroxyethylglycine and 2-thioethylglycine. The repeating units may optionally have an attached side chain. The side chain is represented by the formula-A-L wherein A and L are defined below. "Side chain" is used as it is normally interpreted within the field of polymer chemistry.

Figure 2:
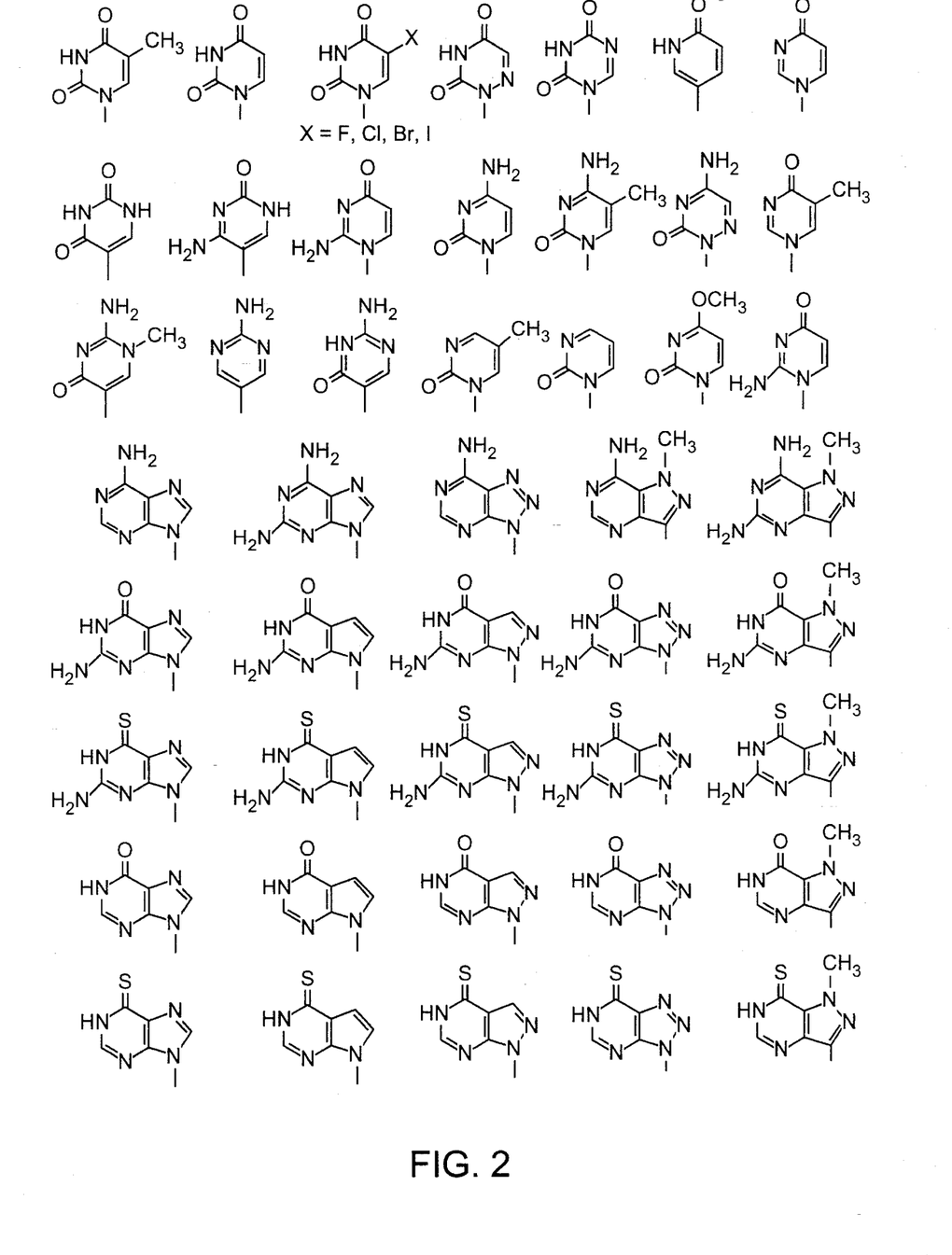
FIG. 2 is a collection of the chemical structures of naturally occurring and non-naturally occurring nucleobases for DNA recognition.

Polymers which are degraded by the method of this invention are PNAs, polyamides, polyesters and polythioesters of the general formula:

The terminal nucleophile is represented by V, wherein, V is independently selected from the group consisting of OH, SH, $NH_2$ and NHR. The atom or group W is the same or different and is selected from the group consisting of H, R, OR, SR, NHR, $NR_2$, F, Cl, Br and I. The heteroatom or alkylated heteroatom is represented by Y wherein each $Y^1$ thru $Y^{q-1}$ is the same or different and is independently selected from the group consisting of O, S, NH and NR. The terminal atom or group is represented by Z wherein, each Z is independently selected from the group consisting of H, OH, OR, $NH_2$, NHR, $NR_2$, SH, SR, any of the 20 naturally occurring amino acids, polypeptides, proteins, DNA oligomers, RNA oligomers, biotin and fluorescein. Amino acids may exist as amides or free acids and are linked to the polymers through their a-amino group thereby forming an amide linkage to the polymers. Likewise, polypeptides and proteins will be linked to the polymers through their a-amino group terminus thereby forming amide linkages. DNA oligomers may be linked to the polymers by their 5' or 3' hydroxyl group thereby forming an ester linkage. RNA oligomers may be linked to the polymer by their 5', 3' or 2' hydroxyl group thereby forming an ester linkage. Alternatively, DNA or RNA oligomers having a terminal 5', 3' or 2' amino group may be linked to the polymer by said amino group thereby forming an amide linkage. Each R is an alkyl group having one to six carbon atoms which may optionally contain a heteroatom or a substituted or unsubstituted aryl group. In one embodiment, R may be a glycan, carbohydrate or sugar moiety. The linking group A connects the ligand L to each backbone repeating unit. Each $A^1$ thru $A^q$ is a single bond, a group of the formula;

or a group of the formula;

Here, W is defined above and each s in an integer from one to five. The ligand is represented by L wherein, each $L^1$ thru $L^q$ is the same or different and is independently selected from the group consisting of W, adenine, cytosine, guanine, thymine, uridine, 5-methylcytosine, 2-aminopurine, 2-amino-6-chloropurine, 2,6-diaminopurine, hypoxanthine, other naturally and non-naturally occurring nucleobases, substituted and unsubstituted aromatic moieties, biotin and fluorescein. The nucleobases are primarily attached at position 9 for purine analogs and position 1 for pyrimidine analogs. Examples of naturally and non-naturally occurring nucleobases represented by L are depicted in FIG. 2. Each m and n is the integer 1 or 2 provided that m does not equal n. In this embodiment, the backbone repeating unit is six atoms in length because degradation is optimized by six membered ring formation.

Figure 1:
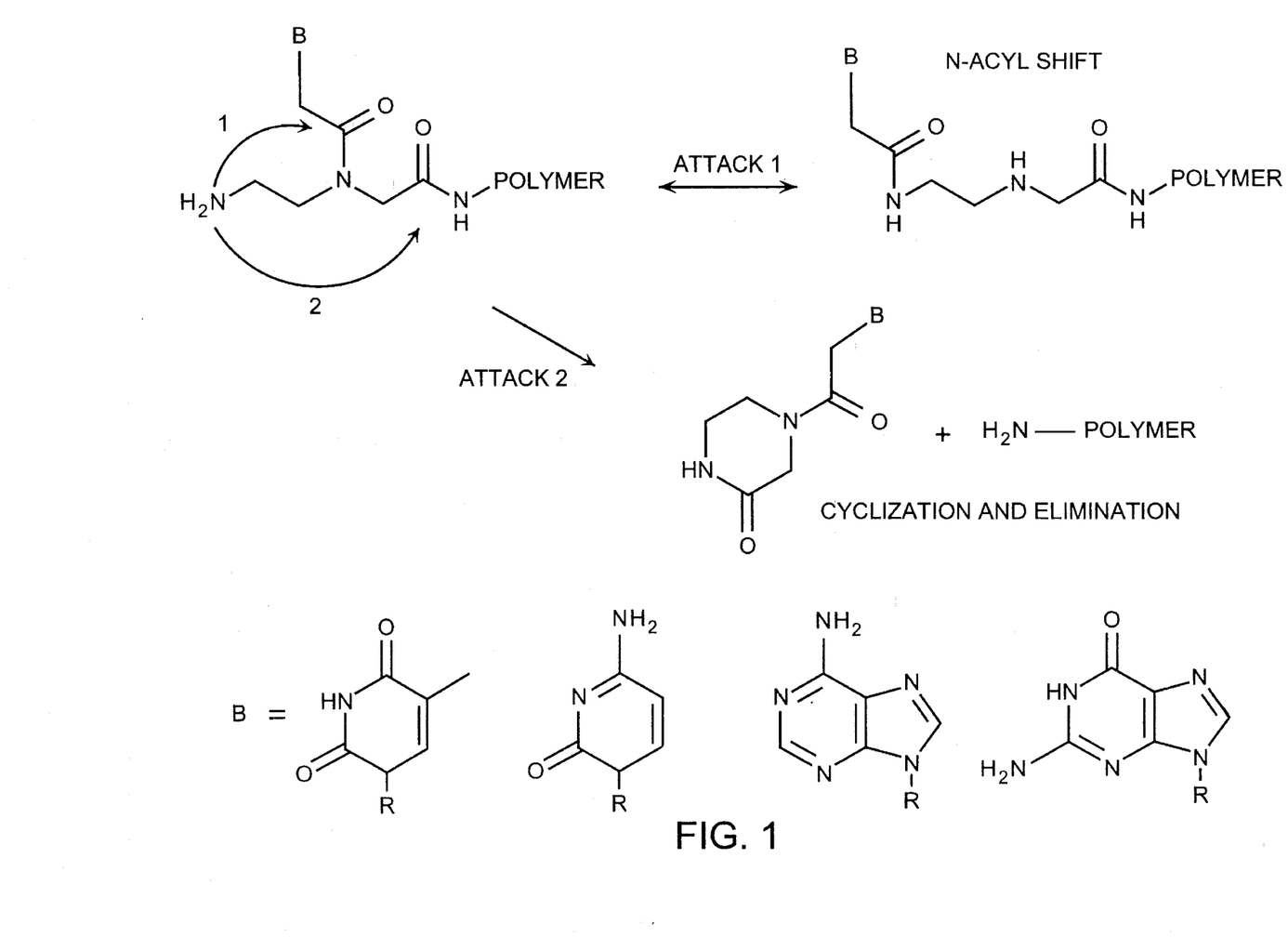
FIG. 1 is a schematic depiction showing the known sites of attack of the terminal nucleophile of PNA.

By the method of this invention the polymer degrades by repeated release of the terminal repeating unit. With reference to FIG. 1, degradation involves the intramolecular attack (under suitable conditions) of the terminal nucleophile (amino, hydroxyl or thiol functional group) of the polymer at the backbone carbonyl carbon five atoms distant from the terminal nucleophile. An example is depicted as "attack 2" in FIG. 1 where the polymer is PNA. In the preferred embodiment, the terminal nucleophile is an amino group. When the terminal nucleophile and the electrophilic carbonyl carbon are separated by 4 atoms, the terminal repeating unit forms a stable six-membered ring which is simultaneously released from the polymer, thereby generating a shortened polymer having additional terminal repeating units. Because the shortened polymer contains all the necessary functional groups, the process will continue on the shorted polymer until it is completely degraded or the sample is put below the activation energy of the decomposition reaction. Other ring sizes, such as 5- and 7-membered rings, although not as favorable kinetically as 6-membered, come within the scope of this invention.

Activation of the nucleophile for attack is a function of the nature of the nucleophile and the immediate chemical environment. Conditions which favor nucleophilic attack are adjustments to p H and/or elevated temperature. Primary amino groups are protonated below pH 10 and are therefore poor nucleophiles. Thus, for a terminal amino group, preferred conditions are of pH greater than 10. Hydroxyl groups and thiol groups are protonated only under extremely acidic conditions. Thus, degradation is expected for hydroxyl and thiol terminating polymers even under conditions of acidic pH. Moreover, lactone formation is favored under acidic conditions but esters and thioesters will hydrolyze at high pH. Therefore, preferred condition of p H for hydroxyl and thiol nucleophiles would be between the pH of 2–10. More preferable conditions for hydroxyl terminating polymers would be a pH of 2–4. For all conditions of favorable pH, elevating the temperature will increase the rate of decomposition. Typical temperatures for terminal amine-initiated attack are within the range of 20° C. to 80° C. The preferred condition is 55° C. Typical temperatures for hydroxy and thiol initiated attack are within the range of 20° C. to 60° C.

Degradation will not occur where the terminal nucleophile is blocked. Protonation is one type of blocking event. Blocking also occurs through the reaction of the terminal nucleophile with a reagent which forms a stable covalent bond. Typical blocking groups are acetyl, benzoyl, Fmoc, t-boc, and trityl. Nonetheless, removal of a blocking group will regenerate a free terminal nucleophile suitable for decomposition. Thus, blocking or selective protection is a means to control the degradation process thereby allowing one to trigger the deprotection reaction by deprotecting the terminal nucleophile.

The terminal amino group of PNA has also been shown to attack at a side chain carbonyl carbon in addition to the backbone carbonyl carbon 5 atoms distant. FIG. 1 depicts both attacking events. Attack at the side chain carbonyl carbon, described as "attack 1", causes an N-acyl shift. This is a covalent blocking event but it is reversible. See Christensen, L. et al., *Optimized Solid-Phase Synthesis of PNA*

*Oligomers,* Thirteenth American Peptide Symposium, Poster No. 7, June 20–23, Edmonton Canada. Thus, degradation will proceed despite transient N-acylation. Nonetheless, N-acylation is a competing reaction that slows the decomposition process of PNA.

In another embodiment of this invention a polymer is sequenced. By the method of this invention a polymer is partially or completely degraded thereby generating a nested set of polymer fragments. The nested set of polymer fragments is comprised of polymer fragments all having a common terminus and each fragment representing a polymer which has been shortened by 1 or more repeating units. Thus, each polymer fragment is comprised of N-x repeating units where N is the total number of repeating units in the parent polymer and x is the number of degradation cycles the polymer has been subjected to. Ideally, the nested set will contain measurable quantities of fragments representing the parent polymer and each of the shortened polymer fragments formed by sequential degradation. Thus, the nested set will define the sequence of the polymer.

The nested set of polymer fragments is then subjected to analysis. In one embodiment, analysis consists of mass analysis. Mass analysis may be obtained using fast atom bombardment mass spectroscopy (FAB-M/S), electrospray ionization mass spectrometry or other mass spectrometry methods. In a preferred embodiment, mass analysis is by matrix assisted laser desorption time-of-flight (MALDI-TOF) mass spectroscopy.

Sequence is determined by calculating the mass differences between all fragments thereby identifying the terminal repeating unit lost to generate each sequentially degraded polymer. Specifically, the identity of the first terminal repeating unit (residue) is determined by the mass difference between the parent polymer and the N-1 polymer. The two species' masses are determined, preferrably by maLD-TOF. The difference is correlated with a specific residue mass, appearing, for example, in Table 1. The second residue and identified by the mass difference between the N-1 and N-2 polymer fragments, in the same manner as just described. The third residue is identified by the relative mass difference between the N-2 and N-3 fragments. Analysis continues in this manner until the primary structure of the polymer is elucidated. However, the sequence of the final two residues of the polymer are typically not identified because background peaks generated by the matrix and the terminal repeating units clutter the mass spectrum in the range of 200 to 500 AMU. In order to assess the last two members of the sequence, a mass off-setting adduct molecule may be linked to the polymer, thereby increasing the mass of the last two polymer fragments so that they are separable from the background of the MALD-TOF mass spectrometer.

TABLE 1

| Nucleobase | Mass of Terminal Repeating Units | | |
| --- | --- | --- | --- |
| | PNA series | Polyester series | Polythioester series |
| A | 275 | 276 | 292 |
| C | 251 | 252 | 268 |
| G | 291 | 292 | 308 |
| T | 266 | 267 | 283 |

Where the polymer has greater than fifteen repeating units, the nested set may not contain measurable quantities of the parent polymer and all possible shorter fragments because the parent might be completely degraded before appreciable amounts of shorter fragments are formed. This obstacle is overcome by sampling the degradation reaction over time. The sample at the first time point can be used to generate the sequence of the first few residues by the method described above. The next time point will be used to identify subsequent residues provided there exists one previously identified polymer fragment. Specifically, there is no ambiguity of sequence even if the parent is no longer detectable because the sequence is known to the previously identified polymer fragment and the remaining sequence can be thereafter elucidated by the method previously described.

The invention may be embodied in an apparatus for automatically performing the polymer degradation and sequence analysis. Many different types of sequencing apparatus are now commercially available. One is the Millipore Model 6625 ProSequencer™ (Millipore Corporation, Bedford, Mass.), which is a protein or peptide gas-phase sequencer using Edman chemistry. (See U.S. patent application Ser. No. 07/893,689, filed Jun. 6, 1992) This application is incorporated herein by reference. Other sequenators are described in U.S. Pat. Nos. 4,065,412 (Dreyer), 4,603,114 (Hood), and 4,704,256, (Applied Biosystems, Inc., Foster City, Calif.), all of which are incorporated herein by reference.

Figure 5:
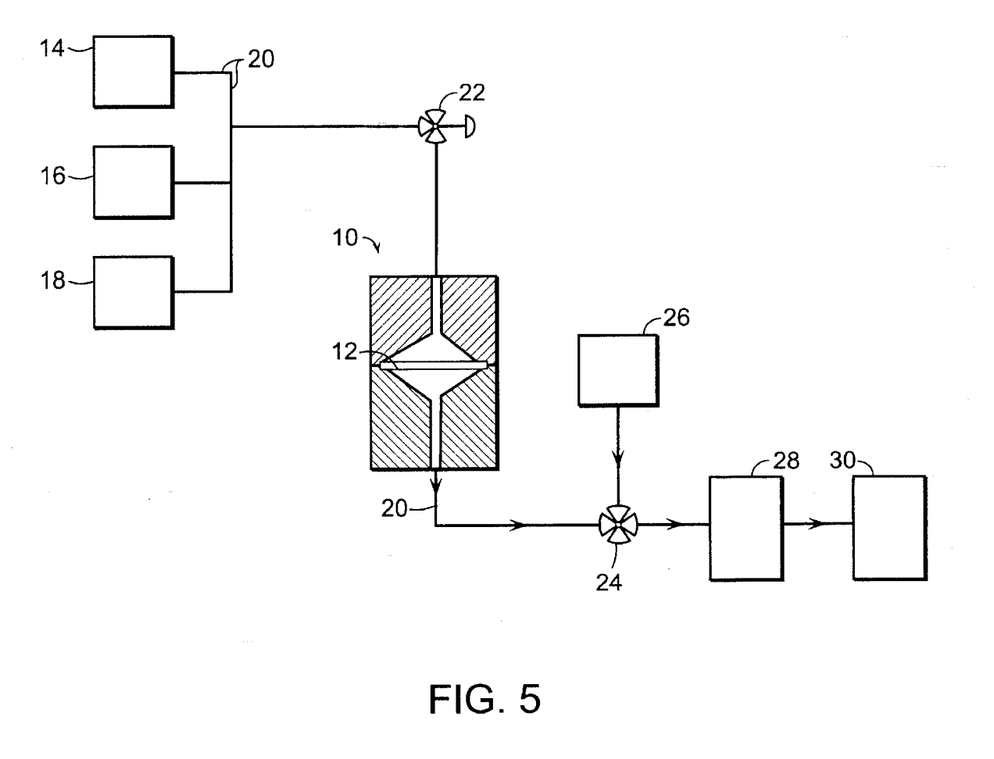
FIG. 5 is a schematic representation of an apparatus for carrying out the method of the invention.

FIG. 5 is a schematic of one possible embodiment of the sequencing apparatus of the present invention. Reaction chamber 10 is located at the center of the schematic. Starting from the left of the schematic, basic vapor 14 and acidic vapor 18 are connected so that they may be introduced into reaction chamber 12 through transfer lines 20 and valve 22. Typical basic vapors include methyl amine, dimethyl amine, and trimethyl amine. Typical acidic vapors include hydrogen chloride, acetic acid, and haloacetic acids such as trifluoroacetic acid. The specific vapor chosen is dependent upon the desired pH that the sample is to be subjected to. Normally, only one vapor at a time will be introduced to control the pH of the polymer sample.

Initiation of nucleophilic attack is partially controlled by the pH of the gases that contact the sample, located on sample support 12, located within temperature-controlled reaction chamber 10. The support may be made from any material that is acid and base resistant. For instance, glass-fiber discs or membranes made from PTFE (polytetrafluroethylene) or polyethylene are suitable. PVDF membranes are also acid and base stable, to a certain extent. Such membranes are available from Millipore Corporation, Bedford, Mass.

Temperature is another condition that may be manipulated to initate cyclization and elimination of the cyclic terminal repeating units. Reaction chamber 10 is fitted with heating elements or jackets in a conventional manner. Thermocouples may be used to monitor and control temperature. Alternatively, temperature control may be monitored and controlled digitally through a computer. Temperature and pH may be varied in order to control the speed of the sequencing reaction.

A nested set of polymer fragments is created under the proper conditions. Transfer buffer 16 may be introduced through lines 20 and valve 22 to contact the sample. Typically, after some period of time sufficient to degrade the polymer as determined by the operator, the transfer buffer will be introduced to wash the reaction products through the system for analysis. Buffer 16 flows through lines 20 and valve 22 to reaction chamber 10, washing the degraded polymer sample off the support 12 and into lines 20. Valve 24 is open to pass the buffer and reaction products onto sample holder 28. Vent 26 is closed during this process, but may be opened for flowing the reactant gasses out of the system. Sample holder 28 is typically made from stainless steel or similar materal suitable for introduction into the high-vacuum atmosphere of a MALD-TOF mass spectrometer, 30. The sample may be dried down with an inert gas such as nitrogen, argon, or helium before introduction into the MALD-TOF.

The transfer buffer contains the ingredients necessary for matrix-assisted laser desorption. Typically, and as detailed in Example 1, this includes sinapinic add and insulin in a water/acetonitrile buffer. The reaction products, when diluted in the transfer buffer, should be concentrated by evaporating the liquid buffer, thereby causing a thin film of crystaline sinapinic acid within which are the analyte reaction products. Laser desorption occurs under the conditions as described in Example 1.

Alternatively, electrospray ionisation MS may be used to analyze the nested set. In this case, sample holder 28 is replaced by the electrospray interface, which is directly attached to a quadrupole mass spectrometer. The technique is described more particularly in U.S. Pat. No. 4,209,696 (Fite), and incorporated herein by reference.

Having now generally described this invention, the same will become better understood by reference to certain specific examples which are included herein for purposes of illustration only and are not intended to be limiting unless otherwise specified. All patents cited herein are fully incorporated by reference.

EXAMPLE 1

A 1 milligram sample of purified PNA having the sequence TTTTCCTCTC (SEQ ID No. 1-lysine amide (provided by Michael Egholm of the University of Copenhagen, Denmark) was dissolved in 300 μl of 0.1% trifluoroacetic acid (TFA) in water. A 2.5 μl aliquot was taken out and the solvent was removed by evaporation under reduced pressure. To the dry sample was added 10 μl of a solution containing 10 mg/ml of 3,5-dimethoxy-4-hydroxy-cinnamic acid (Aldrich Chemical, P/N D13,460-0; hereinafter sinapinic acid) dissolved in 95% aqueous acetonitrile, and 2.0 μl of a 1 mg/ul solution of insulin from bovine pancreas (Sigma Chemical, P/N I-15500; hereinafter insulin) in 0.1% aqueous TFA. The sample was mixed and 1 μl was applied to the sample holder of the maLD-TOF mass spectrometer. The maLD-TOF mass spectrometer which was used was a prototype machine having a linear 50 cm flight tube, a nitrogen laser (337 nm) and a dual channel detector. Ions of interest were subjected to a 30 kV potential. Mass analysis of the sample was acquired and the spectrometer was calibrated using the known masses of sinapinic acid and insulin as internal standards. Because this sample was not subjected to degrading conditions, only the parent polymer ([M+H]= 2748) was observed.

EXAMPLE 2

A 1 milligram sample of purified PNA having the sequence TTTTCCTCTC (SEQ ID No. 1-lysine amide was dissolved in 300 μl of 33% aqueous ammonia (pH 12.5) and the sample was incubated at 55° C. for 100 hours. A 2.5 μl aliquot was taken out and the solvent was removed by evaporation under reduced pressure. To the dry sample was added 10 μl of a solution containing 10 mg/ml of sinapinic acid dissolved in 95% aqueous acetonitrile. The sample was mixed and 1 μl was applied to the sample holder of the maLD-TOF mass spectrometer. Mass analysis of the sample was acquired using the maLD-TOF of example 1 and the spectrometer was calibrated using the known masses of sinapinic acid and the parent ion.

Figure 3:
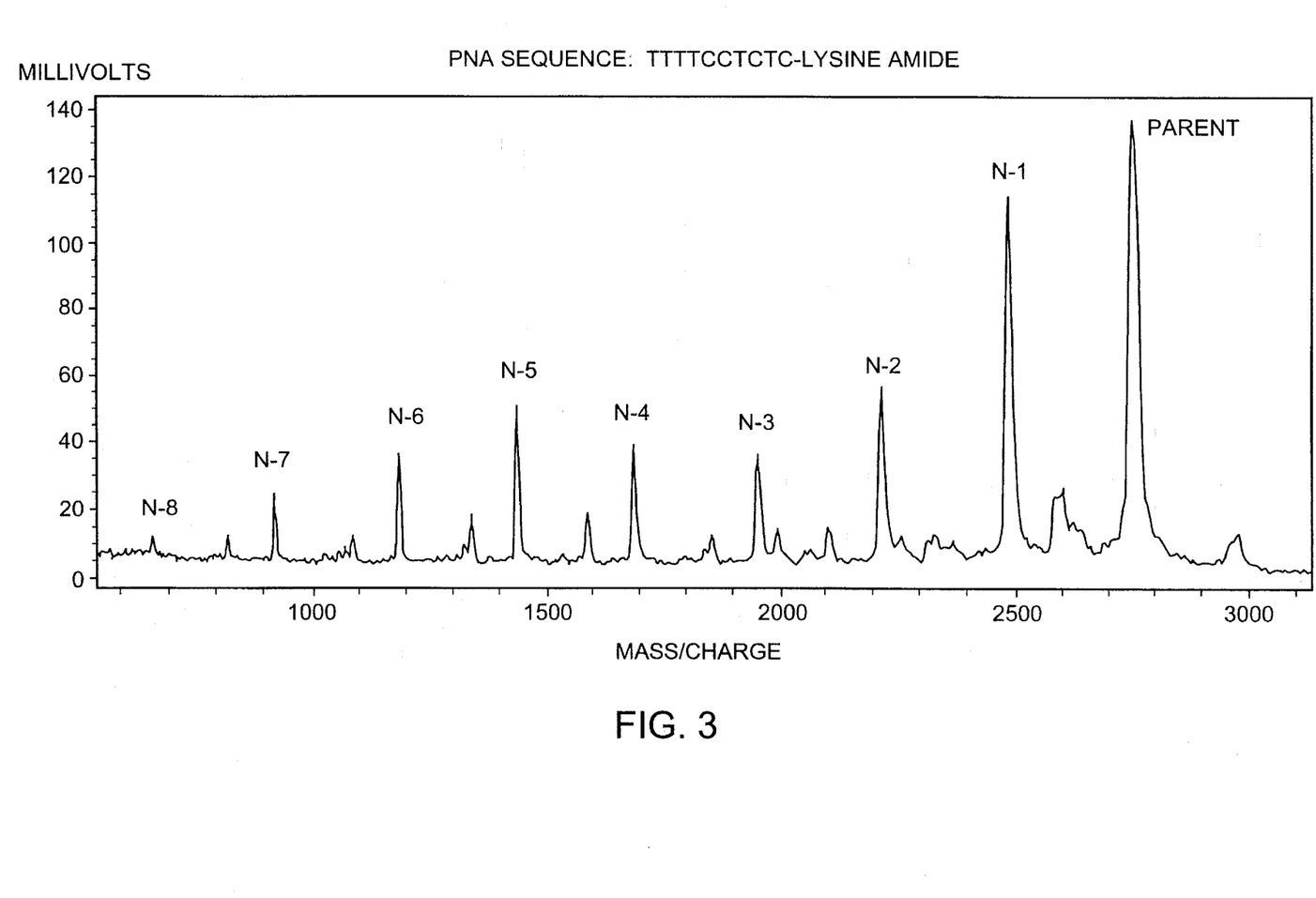
FIG. 3 is the mass spectrum of a nested set of polymer fragments generated by partial degradation of the PNA sequence TTTTCCTCTC-lysine amide.

The spectrum acquired from mass analysis of TTTTC-CTCTC (SEQ ID No. 1-lysine amide after 100 hours of degradation is presented in FIG. 3. Table 1 lists the known masses for each type of PNA terminal repeating unit. Table 2 lists the masses of the fragments observed in the spectrum depicted in FIG. 3.

TABLE 2

| Number of repeating units (N-x) | Number of degradation cycles (x) | Mass of the polymer fragment | Change in mass | Identity of the terminal repeating unit |
|---|---|---|---|---|
| 10 | 0 | 2748.1 | | |
| 9 | 1 | 2481.1 | 267 | T |
| 8 | 2 | 2215.3 | 266 | T |
| 7 | 3 | 1949.7 | 266 | T |
| 6 | 4 | 1683.3 | 266 | T |
| 5 | 5 | 1432.1 | 251 | C |
| 4 | 6 | 1181.3 | 251 | C |
| 3 | 7 | 915.5 | 266 | T |
| 2 | 8 | 664.5 | 251 | C |

N = number of terminal repeating units in the polymer

As expected, the purified parent polymer has a mass of 2747 ([M+H]=2748; See FIG. 3 and Table 2). The N-1 polymer, having undergone one degradation cycle and thereby releasing one terminal repeating unit, has a mass of 2481. The mass difference between the parent and the N-1 polymer is 267. As Table 1 illustrates, the terminal repeating unit having a carboxy methyl thymine (T) side chain has the closest known mass. Because the mass spectrometer has a margin of error of ±1 atomic mass unit (AMU) within this range of masses, there is no ambiguity in the assignment of this residue. Likewise, the N-2 polymer has a mass of 2215. Therefore, the mass difference between the N-1 and N-2 polymers is 266. Consequently, the second residue also contains a carboxy methyl thymine (T) side chain. As Table 2 depicts the analysis may continue until the sequence is elucidated.

EXAMPLE 3

Figure 4:
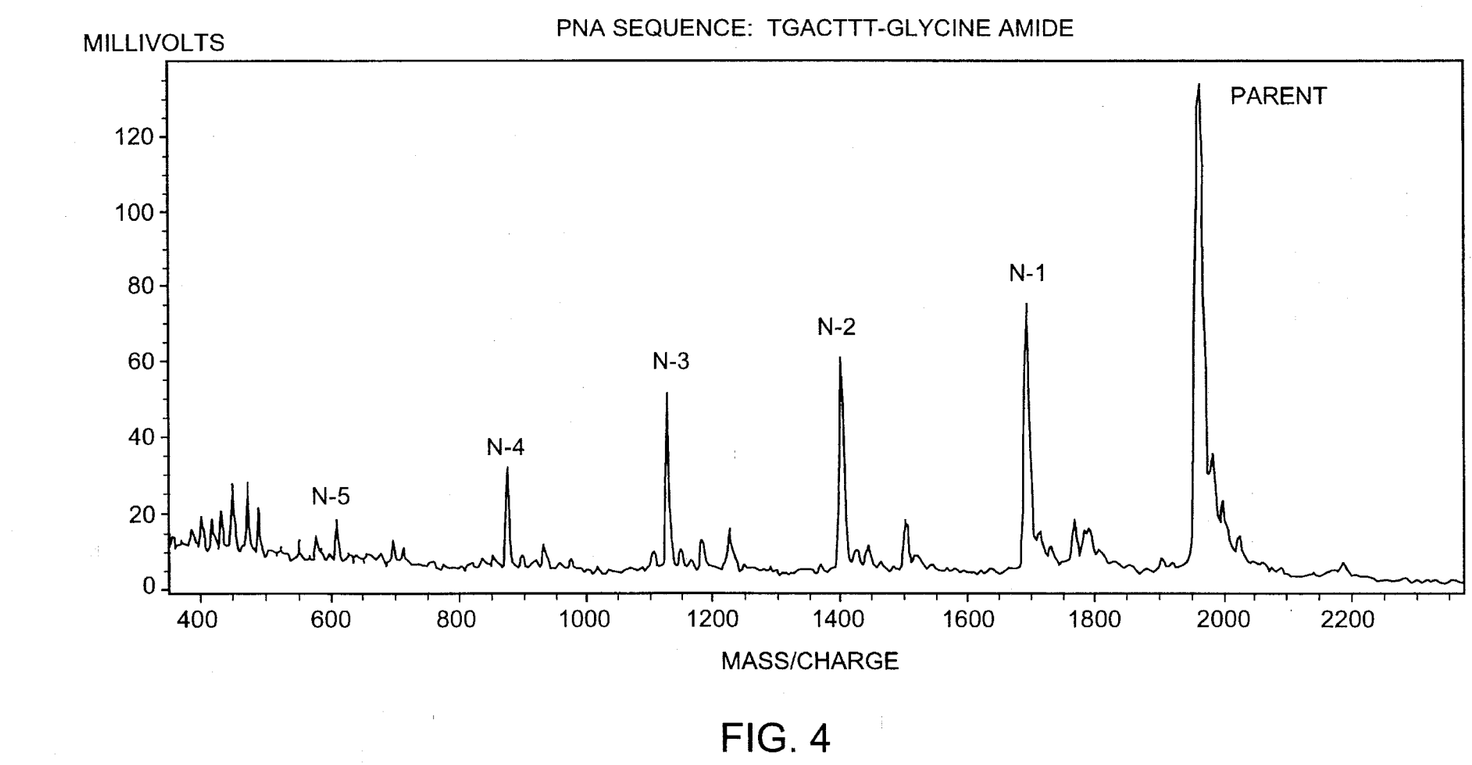
FIG. 4 is the mass spectrum of a nested set of polymer fragments generated by partial degradation of the PNA sequence TGACTTT-glycine amide.

A 1 mg sample of purified PNA having the sequence TGACTTT (SEQ ID No. 2-glycine amide (the polymer was assembled using PNA monomers purcahsed from Millipore Corporation, 80 Ashby Road, Bedford, Mass. 01730; A-monomer P/N GEN063011, Cytosine monomer P/N GEN063013, Guanine P/N GEN063012, and Thymine monomer P/N GEN063010. Synthesis protocols were according to the optimized conditions described in Christensen, L. et al., *Optimized Solid-Phase Synthesis of PNA Oligomers*, Thirteenth American Peptide Symposium, Poster No. 7, June 20–23, 1993, Edmonton Canada) was dissolved in 100 μl of 33% aqueous ammonia (pH 12.5) and the sample was incubated at 55° C. for a total of 48 h. A 2.5 μl aliquot was taken out and the solvent was removed by evaporation under reduced pressure. To the dry sample was added 10 μl of a solution containing 10 mg/ml of sinapinic acid dissolved in 95% aqueous acetonitrile and 2.0 μl of a 1 mg/ml solution of insulin in 0.1% aqueous TFA. The sample was mixed and 1 μl was applied to the sample holder of the MALD-TOF mass spectrometer operated as previously described. Mass analysis of the sample was acquired and the spectrometer was calibrated using the known masses of sinapinic acid and insulin. The spectrum acquired from mass analysis of TGACTTT (SEQ ID No. 2-glycine amide after 48 hours of degradation is presented in FIG. 4. Table 3 lists the masses of the fragments observed in the spectrum depicted in FIG. 4.

TABLE 3

| Number of repeating units (N-x) | Number of degradation cycles (x) | Mass of the polymer fragment | Relative change in mass | Identity of the terminal repeating unit |
|---|---|---|---|---|
| 7 | 0 | 1959.0 | | |
| 6 | 1 | 1692.1 | 267 | T |
| 5 | 2 | 1401.0 | 291 | G |
| 4 | 3 | 1125.5 | 275 | A |
| 3 | 4 | 874.5 | 251 | C |
| 2 | 5 | 608.3 | 266 | T |

N = number of terminal repeating units in the polymer

As expected, the parent polymer had the expected mass of 1958 ([M+H]=1959). The N-1 polymer, having undergone one degradation cycle and thereby releasing one terminal repeating unit, had a mass of 1692. The relative mass difference between the parent and the N-1 polymer was 267. As Table 1 illustrates, the terminal repeating unit having a carboxy methyl thymine (T) side chain had the correct mass. Likewise, the N-2 polymer had a mass of 1401. Therefore, the mass difference between the N-1 and N-2 polymers was 291. Consequently, the second residue contained a carboxy methyl guanine (G) side chain. As Table 3 depicts, by continuing this analysis the third residue contained carboxy-methyl adenine (A), the forth residue contained carboxy-methyl cytosine (C) and the fifth residue contained a caroboxy-methyl thymine (T) side chain. Thus, this experiment demonstrated that the claimed mechanism for degradation and sequencing is valid for all four terminal repeating units found in PNA.

EXAMPLE 4

A 1 mg sample of purified PNA having the sequence TGACTTT (SEQ ID No. 2-lys-lys-lys-lysine amide (wherein lys is the amino acid lysine and the polymer is assembled using peptide and then PNA synthesis chemistries) is dissolved in 100 μl of 33% aqueous ammonia (pH 12.5) and the sample is incubated at 55° C. for a total of 48 h. A 2.5 μl aliquot is taken out and the solvent is removed by evaporation under reduced pressure. To the dry sample is added 10 μl of a solution containing 10 mg/ml of sinapinic acid dissolved in 95% aqueous acetonitrile and 2.0 μl of a 1 mg/ml solution of insulin in 0.1% aqueous TFA. The sample is mixed and 1 μl is applied to the sample holder of the MALD-TOF mass spectrometer operated as previously described. Mass analysis of the sample is acquired using the MALD-TOF of example 1 and the spectrometer is calibrated using the known masses of sinapinic acid and insulin. Table 4 lists the masses of the fragments expected in a mass spectrum of the nested set of fragments generated by degrading the polymer.

TABLE 4

| Number of repeating units (N-x) | Number of degradation cycles (N-1) | Mass of the polymer fragment | Relative change in mass | Identity of the terminal repeating unit |
|---|---|---|---|---|
| 7 | 0 | 2412.6 | | |
| 6 | 1 | 2146.2 | 266 | T |
| 5 | 2 | 1855.0 | 291 | G |
| 4 | 3 | 1579.7 | 275 | A |
| 3 | 4 | 1328.5 | 251 | C |
| 2 | 5 | 1062.2 | 266 | T |
| 1 | 6 | 796.0 | 266 | T |
| 0 | 7 | 529.8 | 266 | T |

N = number of terminal repeating units in the polymer

The parent polymer has the expected mass of 2412 ([M+H]=2413). The N-1 polymer, having undergone one degradation cycle and thereby releasing one terminal repeating unit, has a mass of 2146. The mass difference between the parent and the N-1 polymer is 266. As Table 1 illustrates, the terminal repeating unit having a carboxy methyl thymine (T) side chain has the correct mass. Likewise, the N-2 polymer has a mass of 1855. Therefore, the mass difference between the N-1 and N-2 polymers is 291. Consequently, the second residue contains a carboxy methyl guanine (G) side chain. Continuing this analysis the third residue contains carboxy-methyl adenine (A), the forth residue contains carboxy-methyl cytosine (C), the fifth residue contains a carboxy-methyl thymine (T) side chain, the sixth residue contains a carboxy-methyl thymine (T) side chain and the seventh residue contains a carboxy-methyl thymine (T) side chain. Thus, all residues of the polymer may be identified where a mass offsetting adduct is linked to the polymer.

Example 5

A 1 mg sample of purified polyester having the sequence TGACTTT (SEQ ID No. 2) is dissolved in 100 μl of 0.1M aqueous ammonium trifluoroacetate buffer (pH 2.0) and the sample is incubated at 55° C. for a total of 50 hours. A 2.5 μl aliquot is taken out and the solvent is removed by evaporation under reduced pressure. To the dry sample is added 10 μl of a solution containing 10 mg/ml of sinapinic acid dissolved in 95% aqueous acetonitrile and 2.0 μl of a 1 mg/ml solution of insulin in 0.1% aqueous TFA. The sample is mixed and 1 μl is applied to the sample holder of the MALD-TOF mass spectrometer. Mass analysis of the sample is acquired using the MALD-TOF of example 1 and the spectrometer is calibrated using the known masses of sinapinic acid and insulin. The mass spectrum of the polyester TGACTTT (SEQ ID No. 2) is acquired after 50 hours of degradation. Table 1 lists the known masses for terminal repeating units formed by degrading polyesters.

The parent polymer has an expected mass of 1908 ([M+H]=1909). The N-1 polymer, having undergone one degradation cycle and thereby releasing one terminal repeating unit, has a mass of 1642. The mass difference between the parent and the N-1 polymer is 267. As Table 1 illustrates, the terminal repeating unit having a carboxy methyl thymine (T) side chain has the correct mass. Likewise, the N-2 polymer has a mass of 1350. Therefore, the mass difference between the N-1 and N-2 polymers is 292. Consequently, the second residue contains a carboxy methyl guanine (G) side chain. Continuing with the same analysis, the third residue contains a carboxy-methyl adenine (A) side chain, the forth residue contains a carboxy-methyl cytosine (C) side chain and the fifth residue again contains a carboxy-methyl thymine (T) side chain.

EXAMPLE 6

A 1 mg of purified polythioester having the sequence TGACTTT (SEQ ID No. 2) is dissolved in 100 μl of 0.1M aqueous ammonium trifluoroacetate buffer (pH 2.0) and the sample is incubated at 55° C. for a total of 25 hours. A 2.5 μl aliquot is taken out and the solvent is removed by evaporation under reduced pressure. To the dry sample is added 10 μl of a solution containing 10 mg/ml of sinapinic acid dissolved in 95% aqueous acetonitrile and 2.0 μl of a 1 mg/ml solution of insulin in 0.1% aqueous TFA. The sample is mixed and 1 μl is applied to the sample holder of the MALD-TOF mass spectrometer. Mass analysis of the sample is acquired using the MALD-TOF of example 1 and the spectrometer is calibrated using the known masses of sinapinic acid and insulin. The mass spectrum of the polythioester TGACTTT (SEQ ID No. 2) is acquired after 25 hours of degradation. Table 1 lists the known masses for terminal repeating units formed by degrading polythioesters.

The parent polymer has the expected mass of 2020 ([M+H]=2021). The N-1 polymer, having undergone one degradation cycle and thereby releasing one terminal repeating unit, has a mass of 1738. The mass difference between the parent and the N-1 polymer is 283. As Table 1 illustrates, the terminal repeating unit having a carboxy methyl thymine (T) side chain has the correct mass. Likewise, the N-2 polymer has a mass of 1430. Therefore, the mass difference between the N-1 and N-2 polymers is 308. Consequently, the second residue contains a carboxy methyl guanine (G) side chain. Continuing with the analysis, the third residue contains a carboxy-methyl adenine (A) side chain, the forth residue contains a carboxy-methyl cytosine (C) side chain and the fifth residue contains a carboxy-methyl thymine (T) side chain.

Although the foregoing invention has been described by way of illustration and example for purposes of clarity and understanding, it will be apparent that certain changes and modifications may be practiced within the scope of the invention, as limited only by the scope of the appended claims. For instance, mass analysis methods other than those disclosed herein may serve to identify the polymer fragments, and would be considered to come within the scope of this invention. Also, the formation of energetically-favorable cyclized rings other than those having at least 5 members is also considered to come within the teachings and scope of this invention.

We claim:

1. A method for sequentially degrading at least a portion of a polymer of backbone repeating units, said polymer having a terminal repeating unit comprised of a nucleophile and a backbone carbonyl carbon distant from said nucleophile, comprising:

(a) attacking the backbone carbonyl carbon with the nucleophile, in the absence of an external reagent by raising the temperature or adjusting the pH of the environment surrounding the polymer;

(b) to thereby form a ring comprising said terminal repeating unit, and simultaneously releasing said ring and generating a shortened polymer having a terminal repeating unit capable of nucleophile attack upon said backbone carbonyl carbon; and (c) repeating steps (a) and (b) by maintaining the reaction conditions until at least a portion of the polymer is degraded.

2. The method of claim 1 wherein said polymer is a peptide nucleic acid.

3. The method of claim 1 wherein said polymer is selected from the group consisting of a polyamide, polyester or polythioester.

4. The method of claim 1 wherein said polymer is comprised of polymers having a heterogeneous backbone wherein the functional linkages of the backbone are selected from the group consisting of amides, esters, and thioesters.

5. The method of claim 1 wherein said backbone repeating unit is 2-aminoethylglycine.

6. The method of claim 1 wherein said backbone repeating unit is 2-hydroxyethylglycine.

7. The method of claim 1 wherein said backbone repeating unit is 2-thioethylglycine.

8. The method of claim 1 wherein said nucleophile is an amino group.

9. The method of claim 1 wherein said nucleophile is a hydroxyl group.

10. The method of claim 1 wherein said nucleophile is a thiol group.

11. The method of claim 1 wherein said carbonyl carbon atom is at least 4 atoms distant from said nucleophile.

12. The method of claim 1 wherein said polymer is of the general formula:

wherein, each V is independently selected from the group consisting of OH, SH, $NH_2$ and NHR, each W is the same or different and is selected from the group consisting of H, R, OR, SR, NHR, $NR_2$, F, Cl, Br and I, each $Y^1$—$Y^{q-1}$ is the same or different and is independently selected from the group consisting of O, S, NH and NR, each Z is independently selected from the group consisting of H, OH, OR, $NH_2$, NHR, $NR_2$, SH, SR, any of the 20 naturally occurring amino acids, polypeptides, proteins, DNA oligomers and RNA oligomers, biotin and fluorescein, each R is the same or different and is an alkyl group having one to five carbon atoms which may optionally contain a heteroatom or a substituted or unsubstituted aryl group each of $A^1$—$A^q$ is selected from the group consisting of a single bond, a group of the formula, —$(CW_2)_s$— and a group of the formula, wherein W is defined above and each s is an integer from one to five, each of $L^1$—$L^q$ is the same or different and is independently selected from the group consisting of W, adenine, cytosine, guanine, thymine, uridine, 5-methylcytosine, 2-aminopurine, 2-amino-6-chloropurine, 2,6-diaminopurine, hypoxanthine, other naturally occurring nucleobase analogs, other non-naturally occurring nucleobases, substituted and unsubstituted aromatic moieties, biotin, and fluorescein, n=1–2, m=1–2 provided that m does not equal n, p=0–1,000,000.

13. The method of claim 1 wherein the attack comprises first deblocking the terminal nucleophile of a terminally-blocked parent polymer.

14. The method of claim 1 wherein the temperature of said polymer's immediate environment is raised until substantial nucleophilic attack begins.

15. The method of claim 1 wherein the pH of said polymer's immediate environment is adjusted until substantial nucleophilic attack begins.

16. A method for sequencing at least a portion of a polymer of backbone repeating units, said polymer having a terminal repeating unit comprised of a nucleophile and a backbone carbonyl distant from said nucleophile, comprising the steps of:

(a) attacking the backbone carbonyl carbon with the nucleophile in the absence of an external reagent by raising the temperature or adjusting the pH of the environment surrounding the polymer thereby simultaneously forming and releasing a ring and generating a shortened polymer having a terminal repeating unit capable of nucleophilic attack upon said backbone carbonyl carbon;

(b) repeating step (a) to generate a nested set of polymer fragments, each fragment having N-x repeating units where N is the total number of repeating units in the parent polymer and x is the number of times step (a) is performed; and (c) analyzing said nested set of polymer fragments to determine the polymer sequence.

17. The method of claim 16 wherein said polymer is a peptide nucleic acid.

18. The method of claim 16 wherein said polymer is selected from the group consisting of a polyamide, polyester or polythioester.

19. The method of claim 16 wherein said polymer is comprised of polymers having a heterogeneous backbone wherein the functional linkages of the backbone are selected from the group consisting of amides, esters and thioesters.

20. The method of claim 16 wherein said backbone repeating unit is 2-aminoethylglycine.

21. The method of claim 16 wherein said backbone repeating unit is 2-hydroxyethylglycine.

22. The method of claim 16 wherein said backbone repeating unit is 2-thioethylglycine.

23. The method of claim 16 wherein said nucleophile is an amino group.

24. The method of claim 16 wherein said nucleophile is a hydroxyl group.

25. The method of claim 16 wherein said nucleophile is a thiol group.

26. The method of claim 16 wherein said carbonyl carbon atom is at least 4 atoms distant from said nucleophile.

27. The method of claim 16 wherein said polymer is of the general formula:

wherein,
- each V is independently selected from the group consisting of OH, SH, $NH_2$ and NHR,
- each W is the same or different and is selected from the group consisting of H, R, OR, SR, NHR, $NR_2$, F, Cl, Br and I,
- each $Y^1$—$Y^{q-1}$ is the same or different and is independently selected from the group consisting of O, S, NH and NR,
- each Z is independently selected from the group consisting of H, OH, OR, $NH_2$, NHR, $NR_2$, SH, SR, any of the 20 naturally occurring amino acids, polypeptides, proteins, DNA oligomers and RNA oligomers,
- each R is the same or different and is an alkyl group having one to six carbon atoms which may optionally contain a heteroatom or a substituted or unsubstituted aryl group;
- each of $A^1$—$A^q$ is selected from the group consisting of a single bond, a group of the formula:

and a group of the formula, wherein W is defined above and each s is an integer from one to five, each of $L^1$—$L^q$ is the same or different and is independently selected from the group consisting of W, adenine, cytosine, guanine, thymine, uridine, 5-methylcytosine, 2-aminopurine, 2-amino-6-chloropurine, 2,6-diaminopurine, hypoxanthine, other naturally occurring nucleobase analogs, other non-naturally occurring nucleobases, substituted and unsubstituted aromatic moieties, biotin, fluorescein and other reporter ligands, n=1–2, m=1–2 provided that m does not equal n, p=0–1,000,000.

28. The method of claim 16 wherein initiating attack comprises first deblocking the terminal nucleophile of a terminally-blocked parent polymer.

29. The method of claim 16 wherein the temperature of said polymer's immediate environment is raised until substantial nucleophilic attack begins.

30. The method of claim 16 wherein the pH of said polymer's immediate environment is adjusted until substantial nucleophilic attack begins.

31. The method of claim 16 wherein analysis of the nested set of polymer fragments is by mass spectrometry.

32. The method of claim 31 wherein the mass spectrometer is a matrix-assisted Laser Desorption Time-of-Flight (MALD-TOF) mass spectrometer.

33. The method of claim 16 wherein determining the polymer sequence comprises the steps of:

(a) calculating the mass difference between two N-x polymer fragments;

(b) comparing said mass difference with a table of known masses for terminal repeating units thereby identifying the released terminal repeat unit; and (c) repeating steps a and b until the sequence is determined.

* * * * *

UNITED STATES PATENT AND TRADEMARK OFFICE
CERTIFICATE OF CORRECTION

PATENT NO. : 5,527,675
DATED : June 18, 1996
INVENTOR(S) : James M. Coull and Leif Christensen It is certified that error appears in the above-indentified patent and that said Letters Patent is hereby corrected as shown below:

Claim 32, Column 20, line 41 of that claim after "Time-of-Flight" change "(MALD-TOF)" to read ---(MALDI-TOF)---.

Signed and Sealed this

Third Day of September, 1996

Attest:

BRUCE LEHMAN

Attesting Officer

Commissioner of Patents and Trademarks